(12) United States Patent
Gordon

(10) Patent No.: US 6,443,022 B1
(45) Date of Patent: Sep. 3, 2002

(54) FLUID LEVEL DETECTOR AND METHOD FOR USE WITH AUTOMATED WORKSTATION

(75) Inventor: Steve J. Gordon, Weston, MA (US)

(73) Assignee: Intelligent Automation Systems, Inc., Cambridge, MA (US)

( * ) Notice: Subject to any disclaimer, the term of this patent is extended or adjusted under 35 U.S.C. 154(b) by 0 days.

(21) Appl. No.: 09/483,209

(22) Filed: Jan. 14, 2000

Related U.S. Application Data

(60) Provisional application No. 60/115,818, filed on Jan. 14, 1999.

(51) Int. Cl.[7] .............................. B01L 3/00; G01F 23/00
(52) U.S. Cl. ............................... 73/864.25; 73/864.23; 73/293; 73/290 R
(58) Field of Search ......................... 73/864.24, 864.23, 73/864.25, 293, 290; 386/3, 4.01

(56) References Cited

U.S. PATENT DOCUMENTS

| | | | | |
|---|---|---|---|---|
| 3,448,616 A | * | 6/1969 | Wostl et al. ................... 73/293 |
| 3,741,656 A | * | 6/1973 | Shapiro ........................ 73/293 |
| 4,247,784 A | * | 1/1981 | Henry .......................... 73/293 |
| 4,271,123 A |   | 6/1981 | Curry et al. ................... 422/64 |
| 4,554,839 A |   | 11/1985 | Hewett et al. ............. 73/864.16 |
| 4,730,631 A |   | 3/1988 | Schwartz ...................... 134/155 |
| 4,736,638 A | * | 4/1988 | Okawa et al. ............. 73/864.24 |
| 4,835,707 A |   | 5/1989 | Amano et al. ................ 364/497 |
| 4,873,863 A | * | 10/1989 | Bruhl et al. ................... 73/49.2 |
| 5,443,791 A |   | 8/1995 | Cathcart et al. ............... 422/65 |
| 5,455,008 A |   | 10/1995 | Earley et al. ................ 422/100 |
| 6,040,897 A |   | 3/2000 | Clifford et al. ............. 356/4.01 |
| 6,118,134 A | * | 9/2000 | Justak .......................... 73/293 |

* cited by examiner

Primary Examiner—Hezron Williams
Assistant Examiner—Katina Wilson
(74) Attorney, Agent, or Firm—David J. Powsner; Nutter McClennen & Fish LLP

(57) ABSTRACT

A fluid level detection system includes an illumination source and a photodetector. The illumination source produces a beam at a fixed angle, which the photodetector is adapted to sense as it is reflected from the surface of a fluid. The photodetector varies in accord with the amount of the reflected beam that impinges on it. This amount, in turn, varies with the distance between the surface of the fluid, the illumination source and photodetector. The system can be used, for example, in automated pipetting applications in which it is important to ascertain the position of a pipette tip with respect to fluid contained within a body to provide safe and effective automatic processing of the fluid without the pipette tip contacting the body.

3 Claims, 2 Drawing Sheets

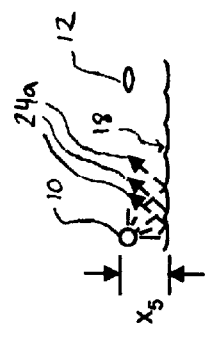
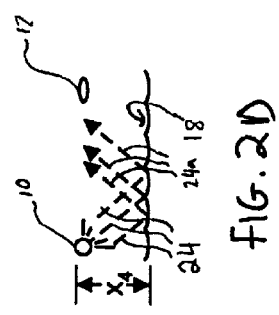
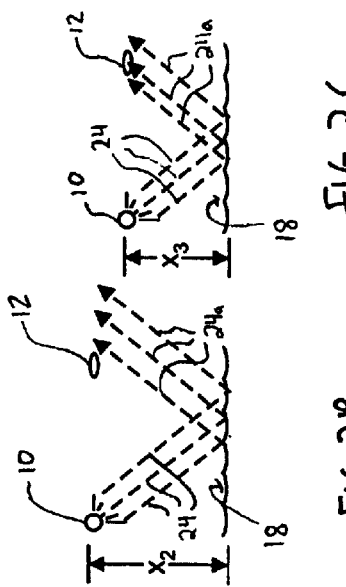
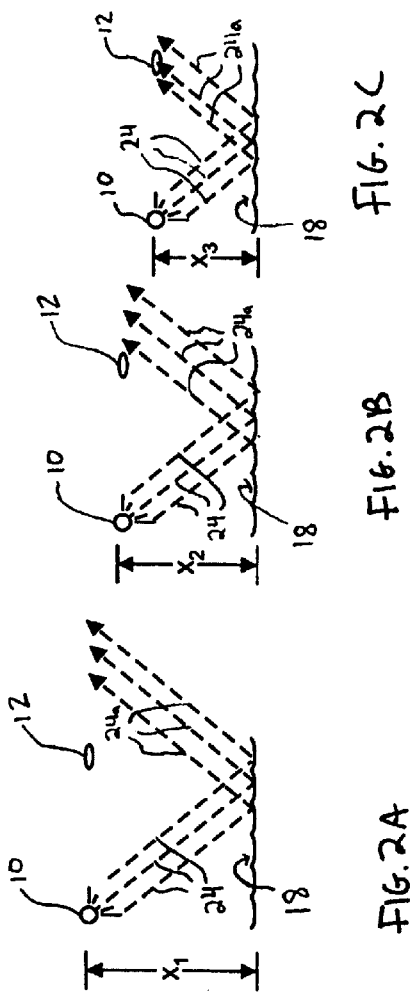
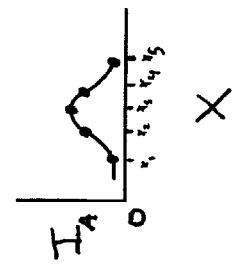
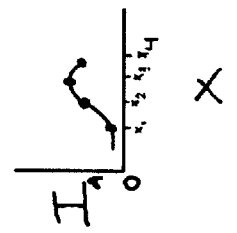
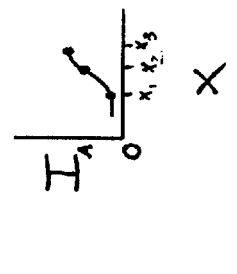
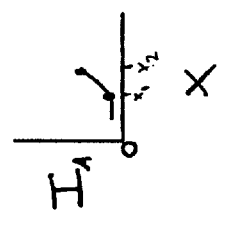
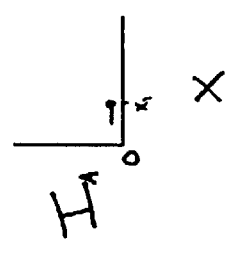

FLUID LEVEL DETECTOR AND METHOD FOR USE WITH AUTOMATED WORKSTATION

CROSS-REFERENCE TO RELATED APPLICATIONS

This application claims priority from U.S. Provisional Patent Application No. 60/115,818, filed on Jan. 14, 1999, which is expressly incorporated by reference herein.

BACKGROUND OF THE INVENTION

This invention relates to automated processing workstations and, more particularly, to methods and apparatus for fluid level detection. The invention has application, for example, in the automated testing, synthesis and processing of biological samples, chemical compounds, and the like.

Historically, nearly all biological and chemical laboratory work was performed manually by scientists and/or laboratory technicians. Recently, however, several factors have made it impractical, if not impossible, to continue to perform the bulk of such work manually. These factors include the tremendous growth of biotechnology and the pharmaceutical industry, and the corresponding demands for increased laboratory throughput and accuracy.

Fortunately, the robotics industry has developed automated equipment and workstations that can be entrusted to handle many laboratory functions. Despite the advantages of such equipment, some functions remain unduly expensive.

One example is pipetting and, in particular, immersing a pipette tip in a fluid. Although this is a routine task when performed manually, it can tax automated processing equipment. In particular, when an individual pipettes a fluid, he or she must ascertain its level in a container in order to ensure that a pipette tip is placed far enough into the container to reach the fluid, yet not too far so as to risk tip and/or container breakage.

Automated pipetting equipment currently available for sensing fluid level is expensive. One system requires pipettes that are equipped with carbon tips. By measuring changes in capacitance, the system can sense fluid at or near the tip. Unfortunately, the carbon tips can be up to 10 times as expensive as conventional plastic tips. Given the frequency with which tips need to be replaced, the increase in tip cost can be unacceptable.

An object of the present invention, accordingly, is to provide improved methods and apparatus for automated processing workstations.

A more particular object of the present invention is to provide an automated workstation capable of continuous, high throughput and high accuracy processing of biological, chemical and other specimens and compounds.

Another object of the present invention is to provide a fluid level sensing system that may be easily implemented or retrofitted into existing automated processing workstations with minimal associated costs. A further object of the present invention is to provide a fluid level sensing system that is compatible with future automated processing workstations.

Yet another object of the present invention is to provide a fluid level sensing system that provides for large-scale pipetting procedures while maintaining acceptable levels of accuracy and safety.

Still another object of the present invention is to provide a fluid level sensing system for use in conjunction with automated pipetting procedures that minimize the risk of damage to equipment and specimens.

Still yet another object of the present invention is to provide a fluid level sensing system that facilitates immersion of pipette tips (or portions of other processing apparatus) in a fluid, yet, prevents risk of breakage of the tips or the containers in which the fluid is disposed.

SUMMARY OF THE INVENTION

The foregoing objects are among those attained by the present invention, which provides a fluid level detection system, e.g., for use in the processing of biological and chemical samples. While the invention is primarily shown and described as pertaining to automated processing procedures such as pipetting, it is applicable to any procedure in which sensing the level of a fluid is desired.

The fluid level detection system of the present invention includes an illumination source and a photodetector, which are aimed toward the liquid and generally angled toward one another. The illumination source produces a beam, which the photodetector is adapted to sense as it reflects from the surface of a fluid. The photodetector output varies in accord with the amount of reflected radiation that impinges on it. That output, in turn, varies as the photodetector (and illumination source) gets closer to the surface of the liquid, increasing then decreasing as the reflected beam moves from overshooting the undershooting the photodetector.

In an exemplary aspect of the present invention, the illumination source and the photodetector are coupled to a pipette tip or other such element. As the tip moves towards the fluid, the photodetector output increases, peaks and decreases to define a pulse-shaped output curve.

The illumination source and the photodetector can be aimed at a point located a predetermined distance, for example, a few millimeters, in front of the tip of the element. This results in the output curve peaking prior to the tip contacting the surface of the fluid. By observing when that peak occurs (and, more generally, by observing the curve itself), the distance between the element tip and the fluid can be readily ascertained.

Further aspects of the invention provide methods of liquid level sensing corresponding to the operations as described above.

BRIEF DESCRIPTION OF THE DRAWINGS

These and other aspects of the present invention will be more fully understood from the following detailed description taken in conjunction with the accompanying drawings, in which:

FIGS. 2A–2E depict an illumination source and a photodetector and their use according to practices of the invention; and FIGS. 3A–3E depict plots of the output of the photodetector of FIGS. 2A–2E as a function of the distance between the photodetector (and illumination source) and the surface of a fluid.

DETAILED DESCRIPTION OF THE DRAWINGS

Figure 1:
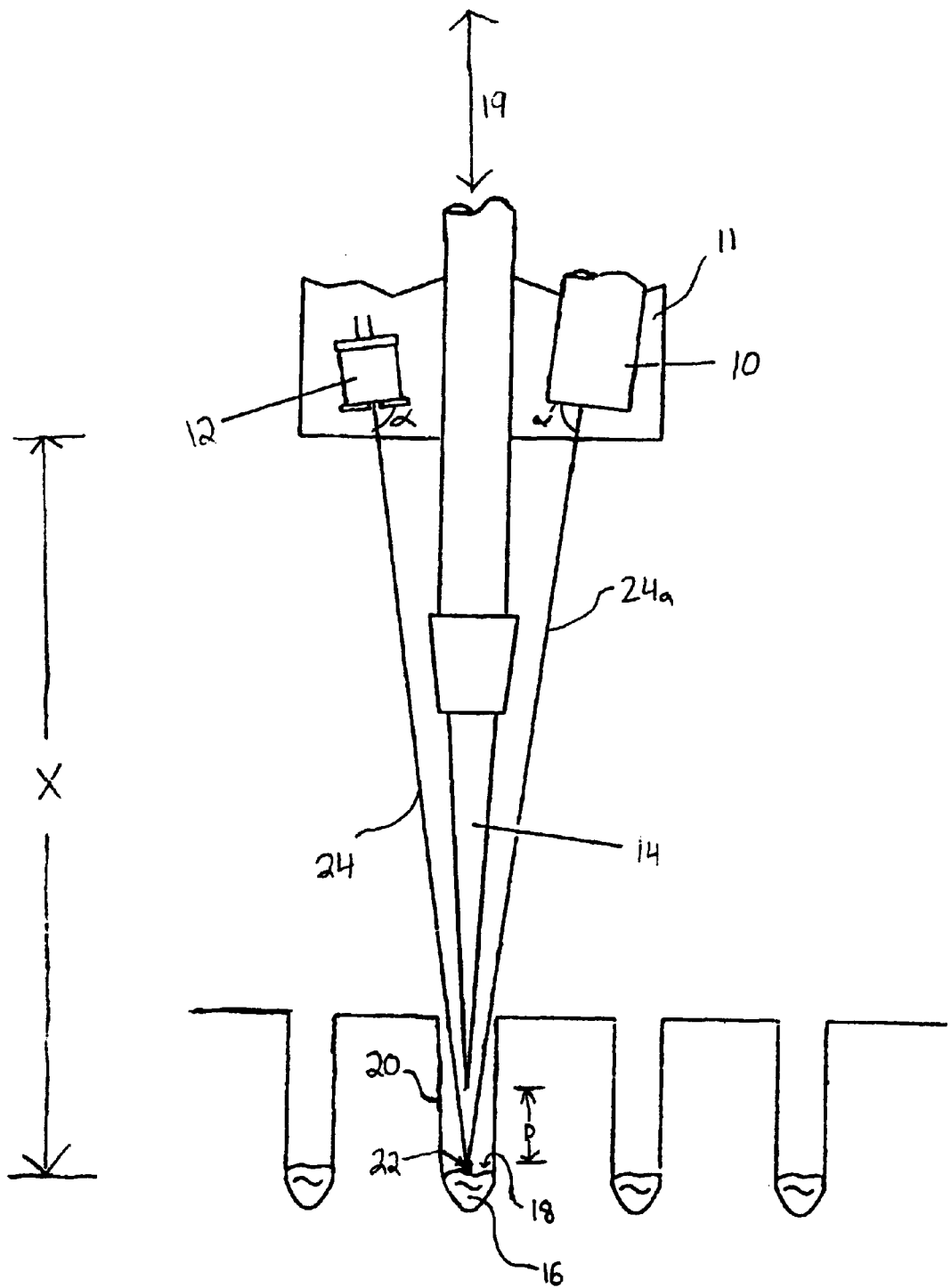
FIG. 1 depicts a pipette tip equipped with a fluid level detection system according to one practice of the invention.

FIG. 1 illustrates a pipetting device incorporating a fluid level detection system according to the present invention. The system includes an illumination source 10 and a photodetector 12 that are arranged to produce an output curve from which can be determined the position of a pipette tip 14 with respect to the surface 18 of a fluid 16 contained within a tube 20.

The illustrated illumination source 10 is disposed on a movable mount 11 and directed at a fixed angle α relative to the surface 18 of the fluid. The angle α is preferably between 45° and 90°, and still more preferably between 60° and 80°, though the specific angle is determined in accord with the requirements and operation of the system. The source 10 comprises any source of illumination, preferably a non-diffuse source, still more preferably a coherent source, and still more preferably, a laser, e.g., a class one diode laser.

The photodetector 12 is also disposed on the mount 11 at a fixed angle α', substantially equal and opposite to angle α (though, again, the specific angle is determined in accord with the requirements and operation of the system). The photodetector 12 is arranged to detect a beam emanating from source 10 and reflected from the surface 18 (e.g., as illustrated by beam paths 24, 24a). An output signal generated by the photodetector 12 is a function of the amount of radiation received by it and, specifically, the amount of the reflected beam 24a that impinges thereupon. The photodetector 12 can be of any type known in the art and, preferably, is a single-bit photodetector, although other such devices can be used instead.

The pipette tip 14 is disposed on the mount 11, as illustrated, for movement with the source 10 and the photodetector 12. In the illustrated embodiment, the tip is disposed between the source 10 and the photodetector 12, though other arrangements may also be suitable depending on the requirements and operation of the system. The illustrated element 14 can comprise the tip of any of the pipetting devices illustrated in U.S. patent application Ser. No. 09/419,179, filed on Oct. 15, 1999, and, particularly, in FIGS. 9–15 thereof and in the accompanying text, which are expressly incorporated by reference. One of ordinary skill in the art will readily appreciate that the invention may be used with any other end effector disclosed in the aforementioned application, or with any other processing apparatus (automated or otherwise) known in the art. For the sake of convenience, terms "pipette tip" and "tip" are used herein, and should be understood to encompass any of the foregoing consistent with the teachings hereof.

Illustrated mount 11 may be fixed, moved manually or, preferably, moved along one or more axes 19 by an automated arm or platform to which it is coupled.

Exemplary such arms and platforms are disclosed in U.S. patent application Ser. No. 09/419,179, filed on Oct. 15, 1999, and, particularly by way of non-limiting example, by FIGS. 7–9 thereof and the accompanying text, which are also expressly incorporated by reference herein.

The tube 20 comprises any well, receptacle, vessel, plate, slide, body or medium (collectively, "tube") for maintaining a fluid to be sensed. In the illustrated embodiment, tube 20 comprises a phial or a well of a microliter plate.

In accordance with an exemplary practice of the present invention, the illumination source 10 is aimed at a point 22 disposed at a predetermined location relative to the illumination source 10 and the photodetector 12. The photodetector 12 is similarly aimed. The term "point, " is used herein for convenience, and should be understood to encompass a point, area or region having any location or size consistent with the teachings hereof.

In the illustrated embodiment, the point 22 is offset by a distance, D, from the distal end of the tip 14 as illustrated. The distance between the point 22 and the tip 14 can be between 0 millimeters (i.e., where the point coincides with the tip) and 50 millimeters, preferably between 1 millimeter and 10 millimeters, still more preferably between 1 millimeter and 5 millimeter, at yet still more preferably approximately 3 millimeters. It will be appreciated that the distance, D, can take on other values, including negative ones (i.e., where the point is proximal to the end of the tip), depending on the requirements and operation of the system.

As the pipette tip 14 is lowered toward the surface 18 of the fluid, the distance X decreases, as does the distance D. The amount of the reflected beam 24a that impinges on the surface of the photodetector 12 and the output of the photodetector changes. The changes in X are shown in FIGS. 2A–2E. The corresponding changes in the output, $I_A$, of the photodetector 12 are shown in FIGS. 3A–3E.

For example, in FIG. 2A, the distance, $X_1$, is relatively large such that the reflected beam 24a overshoots the photodetector 12, thus resulting in a value for $I_A$ of almost zero (as shown in FIG. 3A). In FIG. 2B, the distance, $X_2$ is smaller; accordingly, some of the beam 24a impinges on the photodetector 12, increasing $I_A$ (as shown in FIG. 3B). In FIG. 2C, the distance, $X_3$, is equal to D and, hence, substantially all of reflected beam 24a impinges on the photodetector 12 (as shown by FIG. 3C). As the distance X further decreases, the reflected beam begins to undershoot the photodetector 12 (as shown in FIGS. 2D–2E) thereby causing $I_A$ to decrease (as shown in FIGS. 3D and 3E).

Thus, as the illumination source and photodetector approach the surface of a fluid (i.e., as X is decreased), the amount of reflected beam 24a that impinges on the photodetector will rise, peak, and then fall. The photodetector output (i.e., $I_A$) will likewise rise, peak and fall. By monitoring the resulting pulse-shaped curve, automated apparatus (not shown) can precisely determine the position of the tip 14 relative to the surface of the fluid. Specifically, by knowing the distance between the tip 14 and the illumination source 10 and photodetector 12, in addition to the known characteristics of the pulse-shaped curve (which can be ascertained, e.g., empirically), such automated apparatus can deduce the exact position of the tip 14 with respect to the surface 18 of the fluid. In this manner, the tip can be precisely positioned beneath the surface (or as otherwise desired) without risk of contact with the bottom of the tube 20.

Moreover, it is contemplated that, the illustrated fluid level detection system may also be adapted to detect whether fluid is present in a tube. Particularly, if the aforementioned automated apparatus fails to detect a pulse-shaped photodetection output curve when otherwise expected, the apparatus can signal a "no fluid" condition and take appropriate action.

One skilled in the art will appreciate further features and advantages of the invention based on the above-described embodiments. Accordingly, the invention is not to be limited by what has been particularly shown and described, except as indicated by the appended claims. For example, the terms "tip," "tube," and "point" as used in the claims should be construed beyond their literal meanings as explained above. By way of further example, a fluid level detection system (e.g., comprising an illumination source 10 and a photodetector 12 as disclosed above) can be used in the absence of a tip 14.

In view of the foregoing, what is claimed is:

1. A device for processing biological samples, comprising:

any of a well, receptacle, vessel, plate, slide, phial, body or medium that maintains a sample;

a movable mount;

a pipette that processes the sample and that is coupled to the movable mount for movement relative to the sample;

an illumination source for generating a beam directed at a predetermined point relative to a distal end of the pipette; and a photodetector substantially aimed at the point, the photodetector adapted to sense the beam as reflected from a fluid, and to produce an output representative of an amount of the reflected beam impinging on the photodetector;

at least one of the photodetector or the illumination source are disposed for movement with the pipette, whereby movement of the pipette relative to the sample results in variation of the output of the photodetector; thereby, facilitating detection of a position of the end of the pipette relative to the sample.

2. A device for processing biological samples, comprising:

any of a well, receptacle, vessel, plate, slide, phial, body or medium that maintains a sample;

a movable mount;

an effector that processes the sample and that is coupled to the movable mount for movement relative to the sample;

an illumination source for generating a beam directed at a predetermined point relative to an end of the effector; and a photodetector substantially aimed at the point, the photodetector adapted to sense the beam as reflected from a fluid, and to produce an output representative of an amount of the reflected beam impinging on the photodetector;

at least one of the photodetector or the illumination source are disposed for movement with the effector, whereby movement of the effector relative to the sample results in variation of the output of the photodetector, thereby, facilitating detection of a position of the end of the effector relative to the sample.

3. The device of any of claims 1–2, wherein the output defines a pulse having a peak indicative of coincidence between the point and a surface of the fluid.

* * * * *